(12) United States Patent
Dicks et al.

(10) Patent No.: US 6,197,172 B1
(45) Date of Patent: Mar. 6, 2001

(54) ELECTROCHEMICAL SENSOR WITH GELLED MEMBRANE AND METHOD OF MAKING

(76) Inventors: David H. Dicks, 880 Reynolds Rd., Glocester, RI (US) 02814; Handani Winarta, 18 Hyacinth Dr., Nashua, NH (US) 03062; John Hiti, 5 Fox Run Rd., Danvers, MA (US) 01923; Nicole Pouliot, 633 Moody St., Waltham, MA (US) 02154; Jeffrey C. Chien, 11 New Castle Rd., Ashland, MA (US) 01721; Chung Chang Young, 145 Buckskin Dr., Weston, MA (US) 02493-1166

( * ) Notice: Subject to any disclaimer, the term of this patent is extended or adjusted under 35 U.S.C. 154(b) by 0 days.

(21) Appl. No.: 09/162,478

(22) Filed: Sep. 28, 1998

(51) Int. Cl.[7] ................................................. G01N 27/333
(52) U.S. Cl. ....................... 204/416; 204/415; 205/778.5; 205/789.5; 427/58
(58) Field of Search ................................... 204/415, 416, 204/418, 419; 427/58

(56) References Cited

U.S. PATENT DOCUMENTS

| | | | |
|---|---|---|---|
| Re. 24,222 | * 9/1956 | Patnode et al. | 204/416 |
| 3,470,071 | * 9/1969 | Vertes et al. | 204/432 |
| 3,647,666 | * 3/1972 | Simon et al. | 204/416 |
| 4,272,328 | * 6/1981 | Kim et al. | 204/418 |
| 4,303,408 | * 12/1981 | Kim et al. | 204/418 |
| 4,561,962 | 12/1985 | Kankare . | |
| 4,568,445 | 2/1986 | Cates et al. . | |
| 4,851,088 | 7/1989 | Chandrasekhar et al. . | |
| 4,885,077 | 12/1989 | Karakelle et al. . | |
| 4,986,271 | * 1/1991 | Wilkins | 204/415 |
| 5,132,345 | 7/1992 | Harris et al. . | |
| 5,248,403 | * 9/1993 | Tomita et al. | 204/416 |
| 5,326,449 | 7/1994 | Cunningham . | |
| 5,567,290 | 10/1996 | Vadgama et al. . | |

* cited by examiner

Primary Examiner—T. Tung
(74) Attorney, Agent, or Firm—Robert R. Deleault, Esq.; Mesmer & DeLeault, PLLC

(57) ABSTRACT

An electrochemical sensor with a gelled membrane for prolonging the useful life of an ion-selective electrode. The gelled membrane is a hydrophilic membrane having a specially-formulated gel layer coated on one side. The gel-coated side of the gelled membrane is in intimate contact with the ion-selective membrane and separates the ion-selective membrane from the test samples and the calibration and cleaning fluids. The gelled membrane is a semi-permeable barrier which allows passage of the species to be measured while inhibiting the passage of surfactant and proteinaceous material into the polymeric ion-selective membrane.

27 Claims, 4 Drawing Sheets though permeable to the ions being measured. It is still another object of the present invention to provide an ISE that inhibits the extraction of ionophores and plasticizers from the polymeric membrane. It is yet another object of the present invention to provide an ISE that inhibits surfactant-type agents from entering the polymeric membrane of the ISE.

ELECTROCHEMICAL SENSOR WITH GELLED MEMBRANE AND METHOD OF MAKING

BACKGROUND OF THE INVENTION

1. Field of the Invention

The present invention relates generally to electrochemical sensors.

Particularly, this invention relates to an electrochemical sensor having a prolonged useful life and/or other improved performance characteristics. More particularly, this invention relates to a polymeric membrane ion-selective electrode (ISE) having a prolonged useful life and/or other improved performance characteristics. Even more particularly, this invention relates to an ISE polymeric membrane with a gelled membrane composite boundary between the sample being tested and the polymeric membrane.

2. Description of the Prior Art

The conventional detection of various chemical species customarily uses electrochemical sensors specially designed for determining a particular chemical species' concentration, more accurately described as its activity, in a solution. The determination is based on the fact that within certain limits, the potential of the electrode is directly proportional to the logarithm of the chemical species' activity. These electrochemical sensors generally have sensing membranes specifically formulated for measuring the chemical species of interest. One of the essential properties of an electrochemical sensor is its selectivity. In other words, the results that are obtained are maximally independent of other chemical species/ions which are present in the sample being tested.

Selective membrane sensors originated in the basic pH glass membrane electrode. The advent of crystal and liquid membrane sensors led to the development of ion-selective electrodes. Combining these sensors with microporous synthetic membranes resulted in electrochemical sensors for measuring carbon and sulfur dioxide, ammonia, hydrogen sulfide, and other dissolved gases in blood urine and body fluid samples. Coupling biological reagents to gas sensors and ion-selective electrodes resulted in biosensor systems involving enzymes, bacteria, tissue cells, and immuno-agents. Other types of sensors have also been developed which include affinity, enzyme-linked immunoadsorbent, immune-complex, antigen, and antibody sensors. The ion-selective electrode is the key element of many biosensors.

ISEs have many applications in the fields of medicine, engineering, industrial processing control, education, and research. They are especially useful in clinical and environmental chemistry where large numbers of samples are processed.

Basically, the sensing membrane is made of glass or various polymers such as polyvinyl chloride (PVC), silicone and the like. Sensors using glass membranes such as sensors for pH and sodium are relatively resistant to leaching under normal test conditions. Even when used in media such as human serum containing lipophilic agents, a glass-membrane type sensor can usually be cleaned and reconditioned thus extending the sensor's useful life. A polymeric-membrane type ISE, on the other hand, is more sensitive to the conditions that cause failure, thus having a much shorter useful life as compared to glass-membrane type sensors. One of these conditions is the presence of interfering ions or substances.

Various attempts have been made in the past to couple multiple sensors together and to prolong sensor life.

U.S. Pat. No. 4,568,445 (1986, Cates et al.) discloses an electrode system for an electrochemical sensor for measuring vapor concentration having a plurality of electrically conductive sensing segments isolated from each other. The sensing segments are unencapsulated and are each coated with respective ones of ion conducting sensing materials to characterize each of the segments except one which is used as a reference electrode. The outer surface area of the sensing materials and the reference electrode is coated with a layer of nonaqueous electrolyte which serves as a sorption/desorption medium. The electrolyte is covered by a semipermeable thin film membrane made of silicone.

U.S. Pat. No. 4,851,088 (1989, P. Chandrasekhar et al.) discloses an electrochemical system for the detection of carbon dioxide which includes a single cell chamber exposed to the sample medium through a polymeric barrier membrane, a single set of electrodes and utilizes an aprotic nonaqueous, gelled solvent/electrolyte medium which allows measurement of Carbon Dioxide in the presence of both oxygen and water vapor.

U.S. Pat. No. 5,132,345 (1992, S. J. Harris et al.) discloses an ion-selective polymeric membrane for an electrochemical sensor for use in analytical chemistry. The polymeric membrane is made of a supporting matrix, usually PVC, and an ionophore selected from calixarene or oxacalixarene derivatives.

U.S. Pat. No. 5,326,449 (1994, David D. Cunningham) discloses a sensor device for measuring the concentration of an analyte in solution. The device includes a composite membrane which incorporates a porous membrane containing an immobilized biologically-active protein and at least one other membrane. The other membrane may optionally be a blocking membrane, partly embedded in the porous membrane, which is adapted to exclude low molecular weight interfering species such as ascorbic acid, or it may be a protecting membrane which is useful for preventing high molecular species from fouling the porous membrane. Both a blocking membrane and a protecting membrane may be included in the composite membrane simultaneously.

U.S. Pat. No. 5,567,290 (1996, P. M. Vadgama et al.) discloses sensor devices for examining fluid samples having, between the sample under examination and a detector, a membrane made of polyvinyl chloride in unplasticized form. This membrane material acts as a barrier to paracetamol and sugars but is permeable to hydrogen peroxide and to oxalate.

Therefore, what is needed is an ISE that has a longer uselife and better performance than ISEs currently available. The uselife of an ISE is defined as the length of time an ISE continues to function properly and reliably for its intended use. What is further needed is an ISE that is more easily cleaned during normal operation inhibiting the deposit of proteins and lipid compounds. What is still further needed is a polymeric membrane sensor that allows the passage of the chemical species to be measured while inhibiting the extraction of ionophores and plasticizers out of the polymeric membrane matrix and surfactant-type agents into the membrane matrix.

SUMMARY OF THE INVENTION

It is an object of the present invention to provide an ISE that has a longer uselife and better performance characteristics than comparable ISEs currently available. It is another object of the present invention to provide an ISE that is easily cleaned during operation. It is a further object of the present invention to provide an ISE that inhibits the deposit of proteins and lipid compounds on the selective membrane of the ISE. It is yet a further object of the present invention to provide a polymeric membrane sensor which has a membrane system that allows passage of the chemical species to be measured and inhibits the extraction of ionophores and plasticizers out of the polymeric ISE membrane matrix. Still a further object of the present invention is to provide a polymer ISE which has a sensor membrane system that inhibits the passage of surfactant-type agents into the polymeric ISE membrane matrix.

The present invention achieves these and other objectives by providing a specially-formulated membrane structure that, when used in conjunction with an ISE, prolongs the uselife of the sensor. There are basically three root causes of failure in polymeric ISE type sensors. The first is the loss of ion-selective components. Ion-selective components such as ligands, ionophores, and ion carriers may be leached out of the polymeric ISE membrane. The second is the loss of membrane plasticizers. Again, membrane plasticizers may be leached out of the polymeric membrane. The third is the absorption of lipophilic agents such as surfactants and proteins which change the polymer matrix of the membrane. The absorption of lipophilic agents also enhances the loss of ion-selective components and the loss of membrane plasticizers, the first and second causes of failure. These have been shown to partition into the polymer matrix causing altered responses and quicker extraction of ion-selective components. The present invention addresses the issues caused by the presence of surfactants and/or proteins in the test media.

Surfactants are commonly used in the reagent solution for cleaning purposes and for minimizing air-bubble formation and retention. Depending on the ISE, surfactants can be extracted into the membrane matrix and affect the ISE performance. Protein containing samples such as plasma and serum can also affect ISE performance by either being extracted into the membrane matrix or adsorbed onto the membrane surface. In addition to the above materials, interfering species may cause serious response changes to particular ISEs. Most ISEs have particular selectivity constants. This is a measure of an ISEs response to an interfering species in relationship to its response to the ion being measured. These materials can cause loss of slope value, increased response times and short-term and long-term stability shifts, all leading to sensor failure and inadequate performance.

Electrochemically, several measurable changes occur as the sensors approach failure. These include loss of Nernstian slope value, lengthening response time, and loss of selectivity (increased interferences). Several approaches have been attempted which have yielded slight or no improvement in the active life of the sensor. These approaches include using alternative matrices such as silicone rubber and polyurethane, and miniaturization of the selective membrane surface exposed to the test medium. Ultimately, these approaches do not address the causes listed above and have minimal beneficial effect.

The present invention includes a housing, an internal active electrode suspended in an electrolyte solution contained in the housing, a polymeric ISE membrane sealed to the housing entrapping the electrolyte solution, and the addition of a specially-formulated membrane which significantly improves the active life and performance of an ion-selective electrode. This specially-formulated membrane is placed between the ion-selective electrode and the test medium. The test medium being the test samples, the calibration and system fluids, and the like.

The specially-formulated membrane includes an aqueous-based gel coating on one side. The gel coating is specially formulated to improve the performance of standard ion-selective electrodes when combined with the membrane sheeting. The coupling of the specially-formulated membrane with standard polymeric ISEs improves performance in several ways. It is more easily cleaned during normal operation, thus inhibiting the deposit of proteins and lipid compounds which will cause a chemical change in the polymeric ISE. It acts as a semi-permeable barrier which allows the passage of the species to be measured while inhibiting the passage of surfactant and proteinaceous material into the polymeric ISE.

The electrochemical sensor of the present invention is made by forming an ion-selective membrane to a housing. The housing is filled with an internal electrolyte solution designed specifically for the particular ISE used. An internal reference electrode, preferably a silver-silver chloride electrode, is secured to the housing such that the internal reference electrode is in contact with the internal electrolyte solution.

A specially formulated membrane (modified membrane) is then layered onto the surface of the polymeric ISE. This specially formulated membrane is generally a porous, hydrophilic membrane having a gel coating layer on one side, as described previously. Suitable membranes may be fabricated from polyesters, polyurethanes, polystyrene, polycarbonate, and polyolefins such as polypropylene, polyethylene and polytetrafluoroethylene. A suitable membrane has a preferred pore size of about 0.1 to 1.0 (where pore size indicates the average size in micrometers of the pores) and a thickness of about 8 to 12 micrometers. The gel coating has a thickness of about 0.0003 inches (7.5 micrometers) to about 0.0011 inches (27.5 micrometers). The preferred membrane material is polyester sheeting.

The side of the modified membrane which has the gel layer is brought into intimate contact with the ISE membrane and held in place. Mechanical devices such as a cap (threaded or snap fit or slide fit), O-ring, elastic band, adhesive-backed washer, etc., may be used to hold the modified membrane in place. The modified membrane may also be bonded directly to the ISE. Bonding to the ISE may be achieved by solvent bonding, ultrasonic bonding, "sandwiching" with an adhesive-backed washer, or any other method that will securely hold the modified membrane in intimate contact with the polymeric base membrane.

Another embodiment of this modified membrane is to add a second layer to the gel layer. The second layer is a layer of the ion exchanger used in the ISE membrane. The thickness of this exchanger layer is about 0.010 inch.

The contact between the ISE membrane and the modified membrane may be enhanced by grinding the ISE membrane to a known curvature. This is especially important when the polymeric base membrane is specific for pH, sodium, lithium, or magnesium. The materials used in the manufacture of these ISE membranes are such that the ISE membrane absorbs water over time. Water absorption into the ISE membrane causes swelling of the ISE membrane. When a flat ISE membrane configuration is used, the water-based swelling of the ISE membrane causes the modified membrane to delaminate from its intimate contact with the ISE membrane over time forming fluid pockets between the modified membrane and the ISE membrane. This, in turn, causes various functional anomalies to occur. Mounting the modified membrane over an ISE membrane ground to a known curvature and mechanically fixing the modified membrane to the ISE membrane instead of bonding them together allows the modified membrane to stretch sufficiently enough to compensate for the swelling and still maintain intimate contact with the ISE membrane.

All of the advantages of the present invention will be clear upon review of the detailed description, drawings and appended claims.

DETAILED DESCRIPTION OF THE PREFERRED EMBODIMENT

Figure 1:
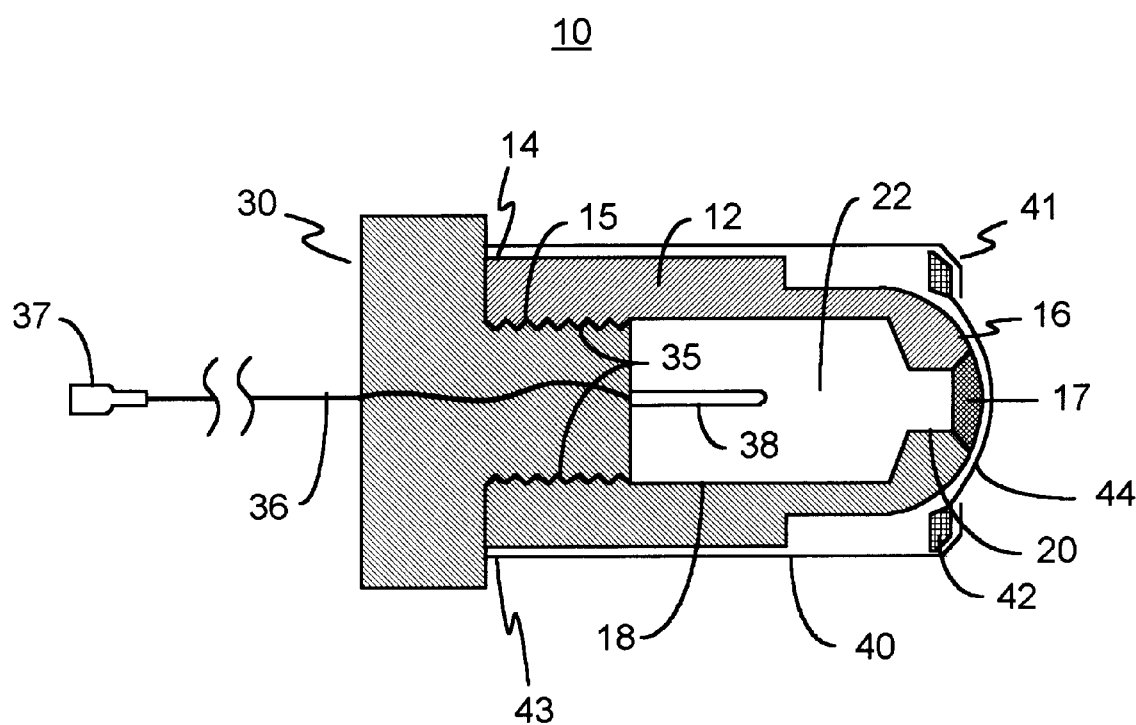
FIG. 1 is a cross-sectional view of the present invention showing an ion-selective electrode with a radius face and a modified membrane cap attached.

The preferred embodiment of the present invention is illustrated in FIGS. 1–4. FIG. 1 shows a sensor 10 of the present invention. Sensor 10 has a body 12, a cap 30, and a membrane housing 40. The body 12 has a first body end 14, a first cavity 18, a second body end 16, a second cavity 20, and an active membrane 17. Active membrane 17 may be any ion-selective membrane formulated for sensing a specific chemical species such as sodium, potassium, chloride, magnesium, lithium, and the like, all as is well known in the art. Second body end 16 has a radius, preferably a radius of 0.5 inches (1.27 cm). Body 12 and cap 30 may be made of any plastic material, preferably polyvinyl chloride (PVC). It should be understood by those skilled in the art that body 12 and cap 30 may be made as a single, unitary piece instead of a two-piece component.

First body end 14 of body 12 has body threads 15 formed on the inside of first cavity 18. First cavity 18 and second cavity 20 are generally filled with an internal electrolyte 22. Internal electrolyte 22 is generally an ionic salt based aqueous solution containing a fixed amount of ions, preferably 0.01 M sodium chloride. However, other electrolytes may be used and such electrolytes are well known to those skilled in the art.

Cap 30 has a first cap end 32 and a second cap end 34. Second cap end 34 has cap threads 35 formed thereon which match threads 15 of first body end 14. It is understood by those skilled in the art that cap 30 may be retained in first body end 14 of body 12 by means other than by threading or in combination. For instance, an adhesive may be use to hold cap 30 in place. Where cap 30 and body 12 are made of comparable plastic material, solvent bonding of cap 30 to body 12 is another alternative. For instance, where the plastic material used is polyvinyl chloride, solvent bonding of cap 30 to body 12 may be performed using tetrahydrofuran. One skilled in the art is capable of determining the solvent required when plastics other than PVC are used. Cap 30 also includes electrical cable 36 having a connector 37 on one end and an active electrode 38 attached on the opposite end. A portion of cable 36 is secured within cap 30 usually by commonly known and used adhesives. Active electrode 38 is preferably a silver-silver chloride electrode, but other redox electrodes may also be used which would be obvious to one skilled in the art.

Membrane housing 40 is tubular with an open end 43 for receiving body 12 and a second housing end 41 containing a modified membrane 44 creating a diaphragm over second housing end 41. Modified membrane 44 is mechanically held in place by washer 42 which has adhesive on one side. Although an adhesive-backed washer is preferably used, any mechanical device used for securing modified membrane 44 in place may be used. Membrane housing 40 is made of plastic, preferably acetal, and is sized to fit over body 12 such that second end 16 protrudes from second housing end 41 causing modified membrane 44 to conform to the radius of second end 16.

Figure 2:
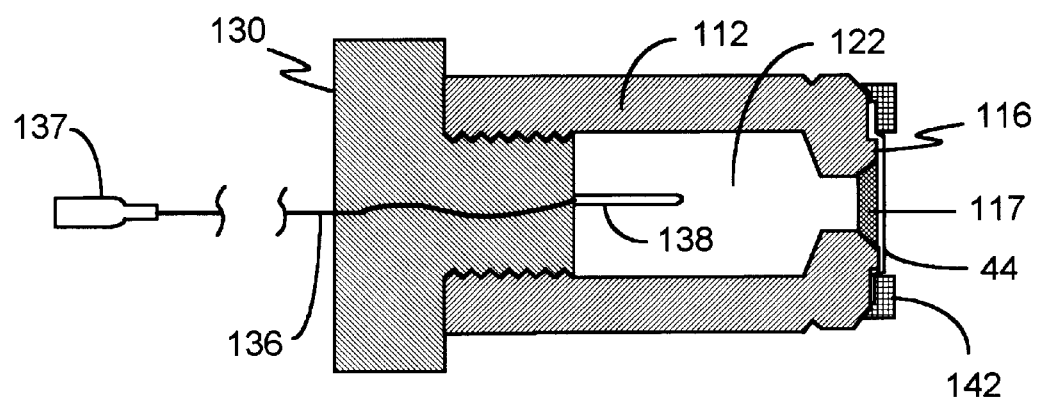
FIG. 2 is a cross-sectional view of the present invention showing an ion-selective electrode with a flat face and a modified membrane bonded to the face of the ion-selective electrode.

A second embodiment of the present invention is illustrated by FIG. 2. An electrochemical sensor 110 has a second sensor body 112, a sensor cap 130 containing a second sensor cable 136 with a second connector 137 on one end and a second active electrode 138 attached to the opposite end, an active sensor membrane 117 formed on a sensor body face 116, and a modified membrane 44. Similarly, as in the first embodiment of the present invention, second sensor body 112 has a second sensor body cavity 118 defined by sensor cap 130 and active sensor membrane 117. Second sensor body cavity 118 contains a second sensor electrolyte 122 having a similar composition as previously discussed. Sensor body face 116 is substantially flat. Modified membrane 44 is secured in place over sensor body face 116 using an adhesive-backed washer 142. Modified membrane 44 may also be bonded directly to sensor body face 116 using tetrahydrofuran solvent, or ion exchange material. Other methods of fixing modified membrane 44 to sensor body face 116 may be used, including but not limited to ultrasonic bonding.

Figure 3:
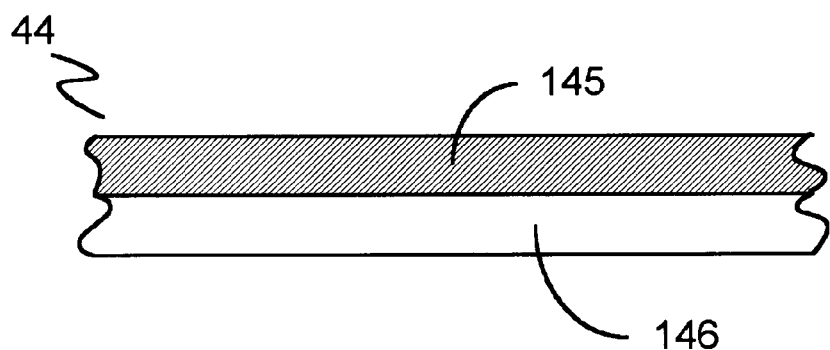
FIG. 3 is an enlarged cross-sectional view of the modified membrane of the present invention showing the relationship of the sheeting material and the gel layer.
Figure 4:
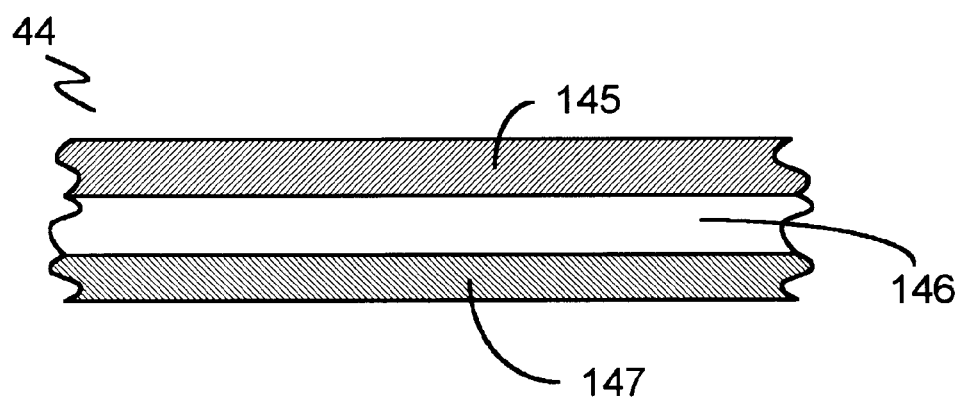
FIG. 4 is an enlarged cross-sectional view of the modified membrane of the present invention showing the relationship of the sheeting material, the gel layer and the ion-exchanger layer.

The use of modified membrane 44, a specially-formulated membrane and a key characteristic of the present invention, is illustrated in FIGS. 3 and 4. FIG. 3 is a cross-sectional view of modified membrane 44 having a membrane layer 145 and a gel layer 146. Membrane layer 145 is generally made from plastic sheeting, preferably polyester, polyethylene or polycarbonate, having an average pore size of about 0.1 micrometers (microns) to about 1.0 micrometers. The sheeting thickness may be in the range of 0.0003 inches (8 micrometers) to 0.010 inches (250 micrometers). Pore size of the sheeting and thickness will affect sensor response time and life expectancy. Gel Layer 146 is has a thickness of about 0.0008 inches (20 micrometers)+/−0.0005 inches (12.5 micrometers). Gel Layer 146 may be aqueous or nonaqueous based, but preferably aqueous based.

FIG. 4 is a cross-sectional view of modified membrane 44 having membrane layer 145, gel layer 146 and exchanger layer 147. The thickness of exchanger layer 147 may be in the range of about 0.001 inches (25 micrometers) to about 0.015 inches (375 micrometers), preferably 0.010 inches (250 micrometers), and is added over gel layer 146. Exchanger layer 147 is generally the same exchanger used in the particular ion-selective membranes 17 and 117 in sensors 10 and 110, respectively. Addition of exchanger layer 147 further enhance the performance life of sensors of the present invention.

Figure 5:
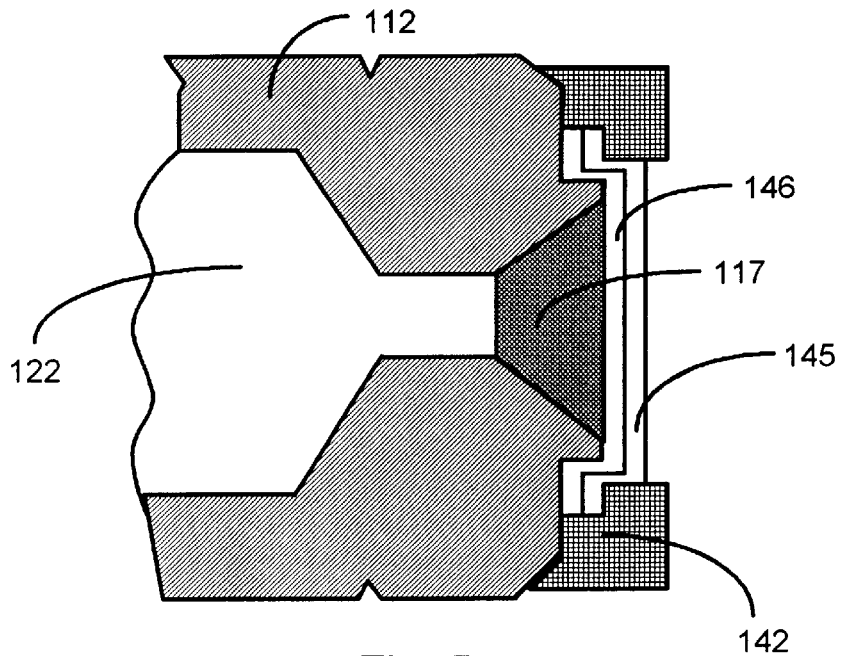
FIG. 5 is an enlarged, cross-sectional view of the sensing end of the present invention shown in FIG. 2 showing the embodiment of the modified membrane of the present invention shown FIG. 3.
Figure 6:
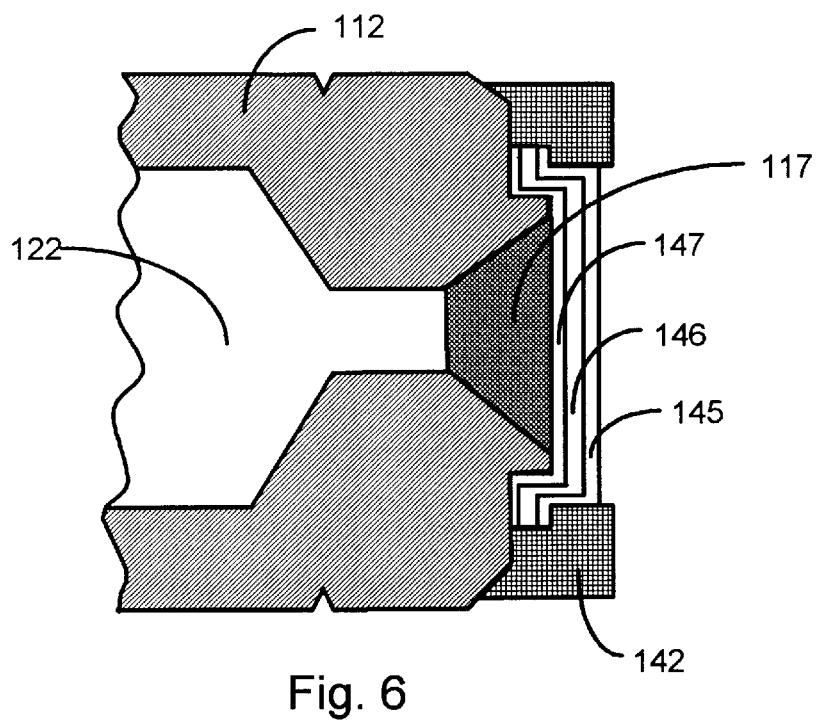
FIG. 6 is an enlarged, cross-sectional view of the sensing end of the present invention shown in FIG. 2 showing the embodiment of the modified membrane of the present invention shown in FIG. 4.

FIG. 5 shows an enlarged, cross-sectional view of the embodiment of the modified membrane 44 shown in FIG. 3 attached to electrochemical sensor 110 shown in FIG. 2. FIG. 6 shows an enlarged, cross-sectional view of the embodiment of the modified membrane 44 shown in FIG. 4 attached to electrochemical sensor 110 shown in FIG. 2.

Gel layer 146 of the specially-prepared modified membrane 44 is made of a phosphate buffer solution (preferably having a pH of approximately 7.4), containing approximately 10% gelatin and approximately 1% glutaraldehyde. The reagents are prepared as follows. One liter of phosphate buffer solution (PBS) of pH 7.4 is prepared with phosphate buffered saline tablets (manufactured by Sigma, cat. #P-4417). The 10% gelatin reagent is prepared by weighing out 1.0 grams of gelatin into a first glass vial and is dissolved with 10 milliliters (ml) of the previously prepared PBS. The glutaraldehyde reagent is prepared by pipetting 250 microliters ($\mu$L) of 8% glutaraldehyde (8% EM Grade from Polyscience, Inc., cat. #00216) into a second glass vial followed by pipetting 1750 $\mu$L of PBS into the same vial. The gluteraldehyde-PBS solution is mixed on vortex for approximately 3–5 seconds.

Modified membrane 44 is prepared in the following way. Begin by placing a piece of polyester (PE) sheeting, represented as membrane layer 145 in FIGS. 3 and 4, having a 0.2 micron pore size onto a glass plate. The pore size represents the average size in micrometers of the pores within the membrane. The polyester membrane sheeting is available from Corning Costar Corporation, cat. #800333. The PE membrane is preferably about 7½ inches (19.05 cm) long by 2 inches (5.08 cm) wide, although any size may be used. Spray the entire surface of the PE membrane with deionized water and blot the excess water from the PE membrane using a piece of technicloth (Technicloth 609 from Fisher Scientific). Allow PE to dry.

Place the first glass vial containing the gelatin inside an oven set at 60° C. until the gelatin has completely dissolved, approximately 15 minutes. Once dissolved, transfer the first glass vial to a second oven set at 37° C. Pipette 750 $\mu$L of the prepared gelatin reagent into a test tube. Pipette 100 $\mu$l of the glutaraldehyde solution into the microcentrifuge tube containing the gelatin reagent. Mix the solutions for approximately 3–5 seconds on the vortex. Immediately pipette 750 $\mu$L of the mixture in the test tube and dispense it along a 0.003 inch (7.5 micrometers) gap doctor blade. Draw the blade across the entire surface of the PE membrane on the glass plate. This drawing of the mixture across the surface of the PE membrane may be performed one or more times, depending on the thickness of the gel layer preferred. Set aside the glass plate with the PE membrane and allow the gelatin mixture to solidify at room temperature. Remove the gel-coated membrane from the glass plate using a peeling action. This is preferably done by placing the glass plate with the gel-coated membrane into a container of distilled water. Using a single edge razor blade, begin gently scraping and lifting one end of the gel-coated membrane from the glass plate. Gently grasp the lifted end with tweezers or fingers and carefully remove the membrane from the glass plate using a peeling motion. Place the gel layer side of the membrane onto a piece of DZ sheet manufactured by Bertex Corporation. Remove excess water by blotting with technicloth. Tape the sides of the membrane to the Bertex sheet with scotch tape and allow to dry.

After drying, modified membrane 44 may be die cut to fit the appropriate embodiment of the present invention. To create modified membrane 44 as illustrated in FIG. 4, a layer of exchanger, preferably 0.010 inch (250 micrometers) thick, is added over gel layer 146. This is also accomplished in a similar way as gel layer 146 was mechanically spread across membrane layer 145.

Several sensors of the present invention containing modified membrane 44 were manufactured and tested against standard sensors without modified membrane 44. Tests were conducted to determine the stability of the sensors in repetitive blood samples using both embodiments illustrated in FIGS. 1 and 2. Tests were performed at 37° C. using a NOVA 18 breadboard system manufactured by Nova Biomedical Corporation. Stability was evaluated by comparing the reproducibility of the sensors' data values in calibrating standards. After sensor calibration, a single standard solution measurement was performed after each sample or series of samples tested. Ion-specific electrodes for chloride, magnesium and sodium were used in the tests.

The following data table represents the test results using Nova Chloride electrodes. It is understood by those skilled in the art that an external reference electrode is required to make all electrochemical measurements described. The Nova 18 breadboard system has a separate external reference electrode that is electrically coupled to the ion-specific sensor being tested. All electrodes had a flat sensor end as shown in FIG. 2. Electrode Nos. 1 and 2 had the modified membrane 44 installed using an adhesive-backed washer, and Electrode Nos. 3 and 4 were standard Nova Chloride electrodes without the modified membrane 44 attached. A total of 851 blood serum samples were tested. The sample trays had a total of 37 samples per tray where the cups numbered 1, 13, 25, and 37 contained a Standard B and all other cups contained serum in a 1:5 dilution diluant is water). After initial calibration, a Standard B solution was measured initially then a new Standard B sample was periodically measured after a given number of blood serum samples to determine electrode stability. The composition of Standard B is given in Table 1. A summary of electrode performance (reproducibility and stability) is given in Table 2.

TABLE 1

Standard B Composition

| Sodium Chloride | 7.6 mM (millimoles) |
|---|---|
| Potassium Chloride | 2.06 mM |
| Sodium Hydroxide | 1.54 mM |
| Sodium Bicarbonate | 4.0 mM |
| Hydrochloric Acid | 1.1 mM |
| Lithium Carbonate | 0.5 mM |
| Tetra Sodium EDTA | 0.23 mM |
| Di-Sodium EDTA | 0.25 mM |
| HEPE | 3.0 mM |
| Glucose | 0.4 g/L (grams per liter) |
| Urea | 0.2145 g/L |
| Creatinine | 0.02 g/L |

TABLE 2

Summary of Standard B Solution Chloride Result at 37° C.
(Readings are in millimoles per liter)

| # of Std. B sample | Elec. #1 | Elec. #2 | Elec. #3 | Elec. #4 | Total # of Serum Samples |
|---|---|---|---|---|---|
| 1 | 56.3 | 57.2 | 54.9 | 55.0 | 1 |
| 10 | 56.3 | 54.4 | 57.6 | 58.3 | 87 |
| 20 | 54.3 | 54.3 | 63.6 | 64.4 | 185 |
| 30 | 54.5 | 53.5 | 64.7 | 70.2 | 272 |
| 39 | 54.1 | 53.6 | 69.9 | 84.5 | 358 |

TABLE 2-continued

Summary of Standard B Solution Chloride Result at 37° C.
(Readings are in millimoles per liter)

| # of Std.<br>B sample | Elec. #1 | Elec. #2 | Elec. #3 | Elec. #4 | Total # of<br>Serum Samples |
|---|---|---|---|---|---|
| 59 | 54.5 | 53.7 | 88.8 | — | 543 |
| 92 | 56.5 | 55.4 | — | — | 851 |
| Avg. | 55.7 | 54.5 | failed | failed | |
| SD | 1.35 | 1.17 | — | — | |
| CV(%) | 2.43 | 2.148 | — | — | |

Avg. = average of all values
SD = standard deviation
CV(%) = coefficient of variation As can be seen from the summary of the data, the results of the electrodes without the modified membrane 44 increase with increasing serum exposure and ultimately failed to function as a useable sensor. The failed sensors could no longer be relied upon to determine accurately the sample chloride concentrations. The electrodes with modified membrane 44 were still working after measuring 851 serum samples.

The use of modified membrane 44 also improved the performance of chloride electrodes in harsh environments where the serum samples also contained surfactants. Table 3 illustrates a comparison of the response between a standard Nova chloride electrode (Electrode #5) and a standard Nova chloride electrode with the modified membrane 44 attached (Electrode #6). As before, all tests were performed on a Nova 18 breadboard system using 37-sample trays with cups 1, 13, 25, 37 containing Standard B and all remaining cups containing blood serum with surfactants. A total of 335 Standard B sample measurements were made. A representative sampling of the data is presented in Table 3.

TABLE 3

Summary of Chloride Test Results at 37° C. under extreme conditions
(Readings are in milligrams per deciliter)

| # of Std. B Sample | Electrode #5 | Electrode #6 |
|---|---|---|
| 1 | 54.5 | 55.5 |
| 40 | 59.9 | 55.7 |
| 80 | 60.6 | 56.6 |
| 120 | 59.9 | 58.1 |
| 160 | 59.3 | 56.8 |
| 215 | 60.5 | 54.6 |
| 220 | —* | 55.6 |
| 280 | — | 55.1 |
| 335 | — | 54.6 |
| Avg. | 59.4 | 55.7 |
| SD | 2.06 | 1.148 |
| CV(%) | 3.462 | 2.061 |

*Electrode unstable

Measurements with Electrode No. 5 were discontinued after Standard B sample No. 215 due to electrode instability. Even in harsh conditions, the electrodes with the modified membrane 44 attached (Electrode #6) out performed the standard electrode without modified membrane 44 (Electrode #5).

Preliminary tests were also performed with a magnesium selective sensor. Two Nova standard production magnesium sensors were used as controls (Electrode #7 and #8). A third electrode having the membrane cap design as illustrated in FIG. 2 (Electrode #9) and a fourth electrode having the integrated membrane design as illustrated in FIG. 1 (Electrode #10) had modified membrane 44 attached. The magnesium tests were performed only in aqueous sample solutions having the compositions L1, L2 and L3 listed in Table 4. After initial calibration, a Standard C was measured between each sample. The low and high voltage values for all Standard C measurements on a given day were obtained for each electrode. The spread between the lowest and highest Standard C value is an indicator of the stability of the sensor under test. A review of the data indicates that both initially and after 14 days, the sensors with the modified membrane 44 (Electrodes #9 and #10) are significantly more stable than the standard manufactured sensors (Electrodes #7 and #8). The composition of Standard C is given in Table 5 and the summary of the test data is given in Table 6.

TABLE 4

Magnesium Sample Compositions

| | L1 | L2 | L3 |
|---|---|---|---|
| NaCl | 114 mM | 88 mM | 78 mM |
| KCl | 6 mM | 4 mM | 2 mM |
| HEPE | 23.8 mM | 20 mM | 13 mM |
| HEPE-Na | 25 mM | 30 mM | 28 mM |
| $CaCO_3$ | 3.83 mM | 3.2 mM | 1.15 mM |
| $NaHCO_3$ | 22 mM | 23 mM | 19 mM |
| HCl | 7.95 mM | 6.625 mM | 2.375 mM |
| Glucose | 0.8 g/L | 2.0 g/L | 3.0 g/L |
| Li Lactate | 0.8 mM | 2.727 mM | 7.576 mM |
| Mg Acetate | 1.2 mM | 0.7 mM | 0.4 mM |
| Urea | 0.214 g/L | 0.535 g/L | 1.07 g/L |

TABLE 5

Standard C Composition

| NaCl | 6.5 g/L |
|---|---|
| KCl | 0.303 g/L |
| NaOH | 32 mM |
| HEPE Acid | 13.24 g/L |
| Li Lactate | 0.194 g/L |
| Glucose | 0.79 g/L |
| Urea | 0.21 g/L |
| $CaCO_3$ | 3.4 g/L |
| $MgCO_3$ | 0.05 g/L |
| HCl | 3.4 mM |

TABLE 6

Summary of Magnesium Test Results

| Standard Sensor | | | | Sensor with Membrane | | | |
|---|---|---|---|---|---|---|---|
| Std C mV Range | | | | Std C mV Range | | | |
| Time<br>(days) | Low<br>Control | High<br>Control | Spread | Time<br>(days) | Low<br>Control | High<br>Control | Spread |
| Elect.<br>#7 | | | | Elect.<br>#9 | | | |
| 1 | 21.6 mv | 24.3 mv | 2.7 mv | 1 | 11.6 mv | 12.5 mv | 0.9 mv |
| 7 | 19.1 mv | 21.8 mv | 2.7 mv | 7 | 11.4 mv | 11.6 mv | 0.4 mv |
| 14 | 17.0 mv | 20.1 mv | 3.1 mv | 14 | 11.7 mv | 12.0 mv | 0.3 mv |
| Elect.<br>#8 | | | | Elect.<br>#10 | | | |
| 1 | 16.8 mv | 18.0 mv | 1.2 mv | 1 | 21.7 mv | 22.1 mv | 0.4 mv |
| 7 | 16.8 mv | 18.4 mv | 1.6 mv | 7 | 14.0 mv | 14.3 mv | 0.3 mv |
| 14 | 1.0 mv | 2.6 mv | 1.8 mv | 14 | 1.8 mv | 2.0 mv | 0.2 mv |

Preliminary tests with polymeric Sodium ISEs were performed. Three Nova sodium sensors were used, two were modified to include the modified membrane 44 and one was the standard sensor used as the control. One of the modified electrodes (Electrode #11) was of the design illustrated in FIG. 2 (flat membrane) and the other modified electrode (Electrode #12) was of the design illustrated in FIG. 1 (radius membrane). Electrode #13 was unmodified and had no modified membrane 44 attached. The three sodium sensors were calibrated in the NOVA 18 breadboard system. After calibration, a Standard C Solution was used for the sodium studies. The standard contains 93 mM NaCl, 4,1 mM KCl, 30 mM NaOH, and 20 mM NaHCO$_3$. Up to ten consecutive readings of the same blood sample were made with each sodium electrode. Consecutive sample measurements were made with each electrode and the millimole concentration of each measurement was recorded. The measurement spread was calculated along with the standard deviation and the coefficient of variation for each electrode. Table 7 contains the sodium sensor test data for the three sodium sensors. Comparing the sensors' respective millimole measurement spread, standard deviation and coefficient of variation, it is obvious, as with the previous ion-selective sensors, that the electrodes containing modified membrane 44 (Electrodes #11 and #12) performed better than the electrode with no modified membrane 44 (Electrode #13).

TABLE 7

Summary of Sodium Sensor Test Data
(Data values are in millimoles per liter)

| Test No. | Elect. #11 | Elect. #12 | Elect. #13 |
|---|---|---|---|
| 1 | 132.9 | 140.0 | 135.6 |
| 2 | 132.5 | 140.6 | 135.5 |
| 3 | 132.2 | 140.0 | 134.1 |
| 4 | 133.4 | 139.9 | 132.9 |
| 5 | 133.8 | 140.3 | 132.1 |
| 6 | 134.0 | 140.3 | 131.0 |
| 7 | 132.9 | 140.3 | 130.9 |
| 8 | 133.8 | 140.2 | 130.1 |
| 9 | 133.5 | 140.2 | 129.8 |
| 10 | — | 140.4 | 128.4 |
| Spread | 1.8 | 0.7 | 7.2 |
| SD | 0.664 | 0.209 | 2.45 |
| C.V.(%) | 0.50 | 0.12 | 1.86 |

It was also found that for anion type ISE electrodes, anion interferences, which are much more troublesome to the uselife of an anion-type ISE, were eliminated or greatly reduced by use of modified membrane 44. Salicylate is a typical example of troublesome interfering ion, especially for the Chloride sensitive ISE. A comparative test was performed using a standard production Chloride electrode (Electrode #14) and a modified Chloride electrode (Electrode #15) having modified membrane 44. The modified electrode had the configuration as shown in FIG. 1. Tests were done by spiking six 120 mM chloride containing solutions with different concentrations of sodium salicylate. The electrodes were calibrated and then each test sample containing a different concentration of the sodium salicylate were measured. The following table, Table 8, shows the results of the chloride electrode measurements of the salicylate-spiked solutions.

TABLE 8

Salicylate Interference Test Results
(Data values are in millimoles per liter)

| Salicylate Concentration | Electrode #14 Modified | Electrode #15 Standard |
|---|---|---|
| 0 | 119 | 120 |
| 1 | 120 | 122 |
| 2 | 121 | 124 |
| 4 | 122 | 132 |
| 6 | 123 | 141 |
| 8 | 125 | 166 |
| 10 | 127 | 218 |

As can be seen from the test results, the use of modified membrane 44 has great reduced the interference effects of salicylate on the measurement of chloride concentrations.

Although the preferred embodiments of the present invention have been described herein, the above descriptions are merely illustrative. Further modification of the invention herein disclosed will occur to those skilled in the respective arts and all such modifications are deemed to be within the scope of the invention as defined by the appended claims.

What is claimed is:

1. An electrochemical sensor comprising:
    a) an active electrode component comprising at least a housing and an active electrode mounted within said housing;
    b) an ion-specific material covering said active electrode component;
    c) a gel layer wherein said gel layer contains a buffer, gelatin and glutaraldehyde, and
    d) at least one porous membrane coated on one side with said gel layer, said gel layer being in communicative contact with said ion-specific material.

2. The electrochemical sensor as claimed in claim 1 further comprising an electrolyte component between said active electrode component and said ion-specific material.

3. The electrochemical sensor as claimed in claim 1 further comprising an ion-exchanger layer between said ion-specific material and said gel layer.

4. The electrochemical sensor as claimed in claim 1 wherein said porous membrane is made of a material that is substantially insoluble in tetrahydrofuran.

5. The electrochemical sensor as claimed in claim 1 wherein said porous membrane is made of a material selected from the group consisting of polyester, polyurethane, polystyrene, polycarbonate, polyethylene, polypropylene, and polytetrafluoroethylene.

6. The electrochemical sensor as claimed in claim 1 wherein said porous membrane has a pore size of less than 1 micrometer.

7. The electrochemical sensor as claimed in claim 6 wherein said porous membrane has a pore size of at least 0.2 micrometer.

8. The electrochemical sensor as claimed in claim 1 wherein said gel layer has a composition of about 10% gelatin and of about 1% glutaraldehyde in a buffer of about 7.4 pH.

9. The electrochemical sensor as claimed in claim 1 wherein said gel layer has a thickness of about 0.0003 inch to about 0.0013 inch.

10. The electrochemical sensor as claimed in claim 1 wherein said ion-specific material is selected to sense a chemical species selected from the group consisting of chloride, sodium, lithium, magnesium, pH, calcium and potassium.

11. A sensor membrane kit for prolonging the useful life of an electrochemical sensor, said kit comprising:
  a) a porous membrane having a gel layer coated on one side, said gel layer containing a buffer, gelatin and glutaraldehyde; and
  b) a housing having two open ends wherein said porous membrane is attached to one of said two open ends, wherein said housing is adapted to be removably connected to said electrochemical sensor such that said gel layer of said porous membrane is in communicative contact with an ion conductive portion of said electrochemical sensor when mounted to said electrochemical sensor.

12. The sensor membrane kit as claimed in claim 11 further comprising a dispenser containing an ion exchanger for applying a controlled quantity of said ion exchanger to said gel layer of said porous membrane prior to removably connecting said porous membrane to said electrochemical sensor.

13. The sensor membrane kit as claimed in claim 11 wherein said porous membrane further includes an ion-exchanger layer covering said gel layer.

14. The sensor membrane kit as claimed in claim 11 wherein said porous membrane has a pore size of at least 0.1 micrometer.

15. The sensor membrane kit as claimed in claim 11 wherein said porous membrane is made of a material that is insoluble in tetrahydrofuran.

16. The sensor membrane kit as claimed in claim 11 wherein said gel layer has a thickness of about 0.0003 inches to about 0.0013 inches.

17. The sensor membrane kit as claimed in claim 11 wherein said porous membrane is made of a material selected from the group consisting of polyester, polyurethane, polystyrene, polycarbonate, and polyethylene, polypropylene, and polytetrafluoroethylene.

18. A method of making a modified membrane electrochemical sensor, said method comprising:
  a) obtaining a porous membrane;
  b) coating one side of said porous membrane with a gel layer whereby said gel layer contains a buffer, gelatin and glutaraldehyde; and
  c) attaching said porous membrane to an ion-specific conductive material portion of an electrochemical sensor wherein said gel layer of said porous membrane is in communicative contact with said ion-specific conductive material portion of said electrochemical sensor.

19. The method as claimed in claim 18 further including the step of adding at least one drop of an ion exchanger to said ion-specific conductive material portion of said electrochemical sensor before attaching said porous membrane to said ion-specific conductive material portion of said electrochemical sensor, said ion exchanger being the same ion-specific chemical used in fabricating said ion-specific conductive material portion.

20. The method as claimed in claim 18 further including the step of applying a thin layer of ion exchanger to said gel layer.

21. The method as claimed in claim 18 wherein said porous membrane has a pore size of about 0.1 micrometer to about 1.0 micrometer.

22. The method as claimed in claim 18 wherein said porous membrane is made of a material that is insoluble in tetrahydrofuran.

23. A coated membrane for prolonging the useful life an electrochemical sensor, said coated membrane comprising:
  a plastic sheet material having a pore size of less than one micrometer; and
  a gel layer coated on one side of said plastic sheet material wherein said gel layer contains a pH buffer, gelatin and glutaraldehyde and wherein said coated membrane is adapted to be attached to said electrochemical sensor with said gel layer toward said electrochemical sensor.

24. The coated membrane as claimed in claim 23 wherein said plastic sheet material is selected from the group consisting of polyester, polyethylene, polypropylene, polycarbonate and polytetrafluoroethylene.

25. The coated membrane as claimed in claim 23 wherein said gel layer contains a buffer of about 7.4 pH, about 10% gelatin and about 1% glutaraldehyde.

26. The coated membrane as claimed in claim 23 further comprising an ion-exchanger layer in communicative contact with said gel layer.

27. The coated membrane as claimed in claim 23 wherein said plastic sheet material has a thickness of at least 0.0003 inch and said gel layer has a thickness of about 0.0003 inch to about 0.0013 inch.

* * * * *